(12) United States Patent
Garcia et al.

(10) Patent No.: US 6,211,143 B1
(45) Date of Patent: Apr. 3, 2001

(54) PREPARATION AND METHOD FOR INCREASING CARTILAGINOUS MASS OF JOINTS IN A MAMMAL

(75) Inventors: Pilar Quijano Garcia, Sant Cugat del Valles; Purificaciò Benavent Quilez, Rubi; Gabriel Espelleta Gil, Premia de Mar; Miquel Junca Riuro; Josep Junca Busquets, both of Banyoles; Ferran Junca Riuro, Porqueres; Jaime Melendo Baños, Cabrils, all of (ES)

(73) Assignee: Masterfarm S.L., Barcelona (ES)

( * ) Notice: Subject to any disclaimer, the term of this patent is extended or adjusted under 35 U.S.C. 154(b) by 0 days.

(21) Appl. No.: 09/194,696
(22) PCT Filed: Mar. 25, 1998
(86) PCT No.: PCT/ES98/00073
§ 371 Date: Nov. 30, 1998
§ 102(e) Date: Nov. 30, 1998
(87) PCT Pub. No.: WO99/48516
PCT Pub. Date: Sep. 30, 1999
(51) Int. Cl.⁷ .................................................. A61K 38/00
(52) U.S. Cl. ...................................................... 514/2
(58) Field of Search ..................................... 514/2

(56) References Cited

U.S. PATENT DOCUMENTS 4,804,745 * 2/1989 Koepff et al. ..................... 530/356

FOREIGN PATENT DOCUMENTS 94 01 887   8/1994   (ES) .
95 00 449   3/1995   (ES) .
95 00 723   4/1995   (ES) .

OTHER PUBLICATIONS

Peripheral Musculoskeletal Untrasound Atlas by S. Marcelis Et Al, 1996, Georg Thieme Verlag Stuttgart, New York, Theme Medical Publishers, Inc.
"Suppression of Type II Collagen–Induces Arthritis . . . ", Nagler–Anderson Et Al, Proc. Natl. Acad. Sci. USA, vol. 83, pp. 7443–7446, Oct. 1986.
Therapie Woche, "Welche Wirkung Haben Gelatinepraeparate", by Adam, pp. 1–6. (1991).
J. Ll. Ribas Fernandez & O. Perez, "Effecto De Los Hidrolizados De Gelatina En La Prevencion De Las Lesiones En . . . ", vol. XV, #66 (1998), pp. 277–282.
"Welche Wirkung Haben Gelatinepraeparate", by Prof. Adam Milan, In Therapie Der Osteoarthrose. (1991).
Bernd Eggergluss: Gelatine Hydrolysate and its Health Aspects, European Food and Drink Review, Fall 1999, pp. 4–8.

* cited by examiner

Primary Examiner—Raymond Henley, III
(74) Attorney, Agent, or Firm—Michael J. Striker

(57) ABSTRACT

A preparation and method for increasing cartilaginous mass of joints in a mammal, especially an athlete practicing a sport, are disclosed. The preparation is administered orally on a daily basis and includes hydrolyzed gelatin having a mean molecular weight of from 10,000 to 50,000 Daltons. The preparation also includes a magnesium-containing organic or inorganic compound and B-group vitamins. A daily dose of the preparation contains from 0.01 g to 2 g of the hydrolyzed gelatin, from 0.002 mg to 1 mg of each B-group vitamin and from 0.25 mg to 15 mg of magnesium, per kilogram of body mass of the mammal.

8 Claims, No Drawings

PREPARATION AND METHOD FOR INCREASING CARTILAGINOUS MASS OF JOINTS IN A MAMMAL

This is a 371 of PCT/ES98/00073 filed Mar. 25, 1998.

BACKGROUND OF THE INVENTION

The subject matter of the present invention includes an orally administered preparation containing highly purified hydrolyzed gelatin enriched with magnesium and B-group vitamins in individuals susceptible to joint injuries caused by excess effort (e.g. athletes), in order to increase the mass of the joint cartilage. This effect was proven by the ultrasonographic measurement of biometric values of the cartilage (thickness).

The injuries derived from the practice of sports represent a health problem due to the considerable requirements that these athletes place on their bodies. Over the last few decades an important increase has been observed in injuries derived from the practice of sports due to the increased number of participants, at a competitive as well as a recreational level, the increase in the number of hours of physical activity, as well as the development of diagnostic methods.

The majority of sports injuries, between 30 and 50%, are due to excessive use, that is to say, they are produced when the demands placed on anatomical structures surpass the tolerance level of the structure involved and repetition of the damaging activity; causing problems in the cartilage by overloading the joints. These types of injuries are more frequent when the athletes do not adhere to an adequate training program, vary their exercise routine, apply sudden changes in the intensity of the force, or do not correctly observe warm-up and/or rest periods. These circumstances often occur in amateur as well as professional competitors.

These problems could be solved by increasing the synthesis of cartilage mass so that the demands placed on the joint are compensated and the tolerance level of the structure is not exceeded. This is the only way to prevent all these joint problems caused by overload and excessive use.

It is well known that the daily ingestion of 5 to 15 g of enzymatically hydrolyzed gelatin has been used as a treatment for the symptoms of arthrosis and other degenerative joint diseases. This improves the general condition of patients affected by these pathologies and the symptoms produced by arthrosis as evaluated by different parameters such as clinical symptomatology (pain), articular mobility, reduction or suppression of the use of analgesics and improvement in limb movement.

These clinical studies and high-priority applications correspond to the following references: Koepff et al. U.S. Pat. No. 4,804,745, Feb. 14, 1989. Therapie der Osteoarthrose. Welche wirkung haben Gelatinepräparate. Adam Milan. Therapiewoche. 38, 2458-2461 (1992).

Although there is considerable speculation about the precise mechanism by which a hydrolyzed collagen can improve the symptomatology of arthritic lesions (e.g. regarding the potential action of glycine-histidine-lysine tripeptide, or modification in the synthesis of type II collagen); it seems that the mechanism could be related to a process of tolerance to proteins ingested by oral route, its effect on the synthesis of cartilaginous matter in these patients being discarded by radiographic studies.

On the other hand, there is a deep belief in the scientific community of the impossibility of generating greater cartilaginous mass by the ingestion of precursors of collagen synthesis, such as hydrolyzed gelatin.

Hydrolyzed gelatin was used to improve the symptomatology in cases of arthrosis or degenerative joint diseases. Even though the pathogenesis of the disease is unknown, in the majority of cases it is related with complex biochemical processes that are based on the synthesis of types of collagen other than the biologically useful type (an increase in the synthesis of type II collagen has been shown to take place in these diseases). At the same time, this can bring about self-immunity processes and the consequent degeneration of the affected joint or joints.

SUMMARY OF THE INVENTION

Surprisingly, the authors of this invention have been able to observe that the continued ingestion of a hydrolyzed gelatin enriched with magnesium and B-group vitamins increases the amount of cartilaginous mass, and this is extremely useful in the prevention of joint injuries caused by over-exertion.

The use of ultrasonography has been established as a reliable method for assessing the integrity and thickness of articular cartilage (ref.: Dondelinger R. F., Marcelis S., Daenen B., Ferrara M. A.: Peripheral musculoskeletal ultrasound atlas. 1996. Thieme Medical Publishers.) and an evaluation has been made of the effect of hydrolyzed gelatin dietary supplements on the ultrasonographic biometric values for the cartilage.

One important point is that gelatin is a protein extracted from the collagen present in the skin and cartilage of animals (mainly pigs, sheep and cattle, as well as fish) and so it contains all the amino acids, and in the same proportions, as required for the synthesis of collagen. Nevertheless, the administration of gelatin as a protein at the required daily dose, established as 0.2 g/Kg a day, would not be feasible since this administration would be quite difficult. This is why the gelatin obtained by extraction from the collagen is submitted to controlled hydrolysis by enzymatic or chemical processes in order to obtain short chain peptides (2000–50000), that can be administered comfortably either dissolved in water or mixed with food, and enable them to be fully absorbed by the organism. In order to improve the body's synthesis of proteins in general and collagen in particular, this substance should be administered in conjunction with magnesium in any of its salt forms (carbonate, citrate, chloride, . . . ) since it acts as a cofactor in numerous enzymatic systems and its presence activates protein synthesis.

Finally, it is also convenient that the administration be combined with various B-group vitamins (B1, B2, B3, B5, B6 . . . ) as adequate doses of these vitamins control the synthesis of proteins in the organism by acting as coenzymes.

As an example, the following is a description of a study proving the efficacy of the present invention. The main active ingredient is a hydrolyzed compound of gelatin, the basis for this patent application.

EXAMPLE 1

The study population consisted of volunteers who were previously informed of the project by means of an informed patient consent form. The population was made up of a men's Mountain Bike (MB) competition team with 16 members (age 24.19±5.23) and a women's basketball team belonging to the honor division of the Spanish Basketball League and consisting of 10 individuals (age 20.30±3.40).

Before the start of the study all the participants provided a complete anamnesis, with special emphasis on any history related to pathologies of the locomotor system. They were then subject to an extensive physical examination to evaluate the condition of their joints and goniometric determinations of the degree of joint mobility. They also underwent an anthropometric study to determine the body composition based on fractionation into four components as well as ergometric and spirometric testing to determine the degree of physical condition.

A first musculoskeletal ultrasonography was performed of the scapulohumeral and femorotibial joints using an ultrasonograph (Concept/MC Ultrasound Scanner) equipped with a 7.5 Mhz transducer. The examination of the shoulder included internal rotation and hyper-extension with the patient in the sitting position. Three measurements were taken in the lateral (HL), medial (HM) and central (HC) zones of the cartilage of the head of the humerus. The measurement of the cartilage of the femoral condyles and the intercondylar notch was carried out with the knee in 70° flexion, the measurements being made at the intercondylar notch (FC) the medial (FCM) and lateral (FCL) condyles. All the measurements were carried out on the right side using the electric caliper of the ultrasonogram. The value taken for the thickness of the cartilage was the mean of the measurements obtained by two technicians at each location.

During the study the athletes continued with their usual training program in their respective sports and they were allowed an unrestricted diet. All the subjects enrolled in the study were provided with a record sheet for them to note all situations which could influence or alter the compliance with the dosage and/or the result of the study. These situations were considered as the appearance of any pain, colds, catarrh, gastroenteric and/or allergic reactions and the administration of any other drugs. The dietary supplement consisted of the ingestion of hydrolyzed gelatin (10 g/dose), enriched with magnesium (160 mg/dose) and vitamins B1 (1.4 mg/dose), B2 (1.6 mg/dose), B5 (6.00 mg/dose) and B6 (2.00 mg/dose) during a period of 6 months.

After six months of treatment they were once again submitted to a second evaluation with review of the incident sheet to determine compliance with the dosage of the treatment, an anthropometric assessment to determine any possible changes in the body composition parameters, and a second ultrasonography to measure the biometric parameters of the cartilage.

Results

The results obtained for the measurements of the thickness of the cartilage in different locations at the start of the study and during the sixth month are shown in Tables 1 to 4. No significant changes were observed in the body composition parameters, although there was a mild increase in the percentages of bone and fat and a mild decrease in the percentage of muscle (Table 5).

The biometric values for the cartilage showed a significant increase in all the measurements for all the individuals with dietary supplements except in the femoral notch, central and lateral scapulohumeral zones. They did show, however, an increase in the cartilage that was not considered significant (Table 6).

After the six month study, the group control did not show any increase in the thickness of the cartilage, quite the contrary, the lateral and medial scapulohumeral locations showed a significant decrease of the biometric measurements for the cartilage.

There was only one case of intolerance to the dietary supplement during the study. This involved the appearance of nausea and vomiting in one basketball player who was later diagnosed for Hepatitis A. The apparent side effects were therefore attributed to this pathology.

Evaluation of the results

Lesions due to excessive effort are acquiring a growing importance in sports medicine. There are many factors that are potentially the cause of these injuries. These may be intrinsic factors, such as incorrect alignment and muscular imbalance, or extrinsic factors, mainly training errors.

There is an enormous number of conditions that could lead to excessive load and strain on joint cartilage, the majority of these are due to malformation of the joint that create an abnormally small contact area. Any increase in the frequency and magnitude of the loads would explain why certain sporting activities involve a high incidence of cartilage degeneration. Processes such as flexion and extension of the knee in cycling or anteversion/retroversion of the arm in basketball, could produce joint strain. Alterations of the cartilage can also be secondary to a molecular attack on the collagen and proteoglycans matrix, as is the case in rheumatoid arthritis or intra-articular hemorrhages. As a result of all this and as can be seen from the results of the present study, the daily supplement of hydrolyzed gelatin could make an important contribution to the prevention of joint strain and injuries to the joint cartilage by increasing the total amount of cartilaginous mass.

TABLE 1

Initial measurement of the joint cartilage MB population

| SUBJECT | HUMERAL | | | FEMORAL | | |
|---|---|---|---|---|---|---|
| | HL | HC | HM | FCL | FC | FCM |
| 1 | 3.9 | 2.7 | 3.7 | 2.8 | 4.4 | 2.8 |
| 2 | 1.6 | 1.3 | 1.5 | 2.9 | 4.2 | 2.9 |
| 3* | 1.3 | 2.3 | 1.7 | 2.3 | 3.5 | 2.0 |
| 4 | 2.5 | 2.5 | 2.7 | 3.1 | 6.0 | 2.2 |
| 5 | 1.8 | 1.9 | 1.6 | 3.4 | 5.9 | 1.7 |
| 6* | 1.5 | 1.2 | 1.7 | 2.2 | 4.3 | 2.6 |
| 7* | 2.0 | 1.9 | 2.3 | 3.2 | 4.8 | 2.5 |
| 8* | 2.0 | 1.6 | 1.3 | 2.1 | 3.6 | 2.1 |
| 9* | 1.7 | 1.6 | 1.9 | 2.7 | 4.0 | 1.6 |
| 10* | 2.3 | 1.6 | 2.8 | 3.0 | 3.7 | 2.5 |
| 11 | 2.2 | 1.7 | 1.8 | 3.1 | 4.9 | 2.4 |
| 12 | 2.3 | 1.9 | 2.7 | 2.2 | 5.8 | 2.0 |
| 13 | 1.6 | 1.3 | 2.3 | 2.4 | 3.2 | 3.0 |
| 14 | 1.4 | 1.9 | 1.4 | 2.5 | 4.6 | 1.9 |
| 15 | 1.8 | 1.6 | 2.2 | 3.0 | 4.6 | 2.9 |
| 16 | 1.7 | 1.7 | 1.9 | 2.6 | 3.2 | 2.4 |

*Subjects with dietary supplement

TABLE 2

Second measurement of the joint cartilage MB population

| SUBJECT | HUMERAL | | | FEMORAL | | |
|---|---|---|---|---|---|---|
| | HL | HC | HM | FCL | FC | FCM |
| 1 | 1.8 | 1.9 | 2.1 | 3.0 | 2.7 | 2.4 |
| 2 | 1.7 | 1.7 | 1.5 | 2.8 | 3.7 | 2.6 |
| 3* | 1.6 | 1.5 | 2.1 | 2.0 | 3.8 | 2.7 |
| 4 | 1.8 | 2.4 | 2.0 | 2.6 | 3.9 | 3.5 |
| 5 | 1.2 | 1.1 | 1.9 | 2.8 | 3.9 | 2.6 |
| 6* | 1.5 | 1.3 | 1.8 | 2.8 | 2.8 | 2.1 |
| 7* | 1.6 | 2.1 | 1.9 | 3.0 | 5.0 | 2.8 |
| 8* | 2.2 | 2.4 | 2.6 | 2.3 | 3.4 | 3.0 |
| 9* | 1.8 | 1.9 | 2.3 | 2.7 | 4.1 | 2.3 |
| 10* | 1.9 | 2.2 | 3.3 | 2.8 | 5.3 | 2.8 |

TABLE 2-continued

Second measurement of the joint cartilage MB population

| | HUMERAL | | | FEMORAL | | |
|---|---|---|---|---|---|---|
| SUBJECT | HL | HC | HM | FCL | FC | FCM |
| 11* | 1.5 | 1.5 | 2.0 | 2.7 | 3.1 | 2.0 |
| 12 | 1.3 | 1.9 | 1.5 | 3.6 | 3.7 | 2.7 |
| 13 | 1.9 | 1.5 | 2.3 | 2.7 | 4.0 | 3.1 |
| 14 | 1.5 | 2.1 | 1.3 | 2.1 | 2.6 | 1.8 |
| 15 | 1.9 | 1.5 | 2.0 | 3.0 | 4.2 | 2.9 |
| 16 | 1.5 | 1.3 | 1.9 | 2.6 | 3.3 | 2.4 |

*Subjects with dietary supplement

TABLE 3

Initial measurement of the joint cartilage Basketball population

| | HUMERAL | | | FEMORAL | | |
|---|---|---|---|---|---|---|
| SUBJECT | HL | HC | HM | FCL | FC | FCM |
| 1* | 1.8 | 1.7 | 3.4 | 3.4 | 4.3 | 3.6 |
| 2* | 1.5 | 2.2 | 2.8 | 2.9 | 3.2 | 2.8 |
| 3 | 1.7 | 2.0 | 2.1 | 2.5 | 2.8 | 2.3 |
| 4* | 1.5 | 1.8 | 2.0 | 2.9 | 2.8 | 2.7 |
| 5* | 1.6 | 2.4 | 2.7 | 2.3 | 4.4 | 3.0 |
| 6 | 1.6 | 2.1 | 2.5 | 3.2 | 3.2 | 2.6 |
| 7 | 2.1 | 2.0 | 2.8 | 2.1 | 3.1 | 2.8 |
| 8* | 1.3 | 1.9 | 2.5 | 3.1 | 4.9 | 3.1 |
| 9 | 1.6 | 1.5 | 2.1 | 1.6 | 3.4 | 1.7 |
| 10 | 2.3 | 1.9 | 2.3 | 2.0 | 3.8 | 2.8 |

*Subjects with dietary supplement

TABLE 4

Second measurement of the joint cartilage Basketball population

| | HUMERAL | | | FEMORAL | | |
|---|---|---|---|---|---|---|
| SUBJECT | HL | HC | HM | FCL | FC | FCM |
| 1* | 2.8 | 2.1 | 3.2 | 3.2 | 5.2 | 3.6 |
| 2 | 2.6 | 2.3 | 2.3 | 2.9 | 4.9 | 3.8 |
| 3 | 1.9 | 2.2 | 2.5 | 3.7 | 3.4 | 3.0 |
| 4* | 2.0 | 2.0 | 2.3 | 3.9 | 4.9 | 2.8 |
| 5* | 1.8 | 2.6 | 2.6 | 2.3 | 4.5 | 3.6 |
| 6 | 1.5 | 1.7 | 2.6 | 2.8 | 3.3 | 2.6 |
| 7 | 1.6 | 2.3 | 2.5 | 2.8 | 4.3 | 2.8 |
| 8* | 2.0 | 2.3 | 2.7 | 3.3 | 4.9 | 4.0 |
| 9 | 1.9 | 1.6 | 2.0 | 1.8 | 3.4 | 1.7 |
| 10 | 1.3 | 1.7 | 2.0 | 3.0 | 5.4 | 3.0 |

*Subjects with dietary supplement

TABLE 5

Body composition values (first and second measurement)

| | FIRST MEASUREMENT | SECOND MEASUREMENT |
|---|---|---|
| Fat | 10.6875 ± 1.114 | 11.0125 ± 1.201 |
| Muscle | 47.4625 ± 1.989 | 46.9500 ± 1.621 |
| Bone | 17.7750 ± 1.323 | 17.9875 ± 1.312 |

TABLE 6

Group with dietary supplement

| | FIRST MEASUREMENT | SECOND MEASUREMENT |
|---|---|---|
| FC | 4.0333 ± 0.685 | 4.2333 ± 0.855 |
| FCL | 2.7667 ± 0.438 | 3.5250 ± 1.020* |
| FCM | 2.5750 ± 0.533 | 2.9083 ± 0.633* |
| HC | 1.8250 ± 0.341 | 2.0250 ± 0.403 |
| HL | 1.7250 ± 0.336 | 1.9917 ± 0.408 |
| HM | 2.2417 ± 0.610 | 2.5583 ± 0.545* |

*= $p < 0.05$

TABLE 7

Control group

| | FIRST MEASUREMENT | SECOND MEASUREMENT |
|---|---|---|
| FC | 4.1571 ± 1.109 | 3.7000 ± 0.701 |
| FCL | 2.5929 ± 0.509 | 2.8071 ± 0.492 |
| FCM | 2.4286 ± 0.465 | 2.6429 ± 0.454 |
| HC | 1.8786 ± 0.398 | 1.7786 ± 0.379 |
| HL | 1.9929 ± 0.639 | 1.6786 ± 0.236* |
| HM | 2.2714 ± 0.604 | 1.9729 ± 0.365* |

*= $p < 0.05$

What is claimed is:

1. A method of increasing cartilaginous mass in joints of a mammal, said method comprising orally administering an effective amount of hydrolyzed gelatin to said mammal, wherein said hydrolyzed gelatin has a mean molecular weight range of from 2,000 to 100,000 Dalton.

2. The method as defined in claim 1, wherein said orally administering occurs daily at a daily dose of from 0.01 g to 2 g of said hydrolyzed gelatin per kilogram of body mass of said mammal.

3. The method as defined in claim 1, wherein said mean molecular weight range is from 10,000 to 50,000 Dalton.

4. The method as defined in claim 3, wherein said orally administering occurs daily at a daily dose of from 0.05 g to 0.5 g of said hydrolyzed gelatin per kilogram of body mass of said mammal.

5. The method as defined in claim 1, further comprising orally administering a daily dose of from 0.002 mg to 1 mg of at least one B-group vitamin per kilogram of body mass to said mammal and wherein said at least one B-group vitamin is selected from the group consisting of vitamin B1, vitamin B2, vitamin B5 and vitamin B6.

6. The method as defined in claim 1, further comprising orally administering a daily dose of from 0.25 mg to 15 mg of magnesium in a magnesium-containing organic or inorganic compound per kilogram of body mass to said mammal.

7. A method of increasing cartilaginous mass in joints of a mammal, said method comprising orally administering to said mammal daily a treatment composition, wherein said treatment composition includes hydrolyzed gelatin, vitamin B1, vitamin B2, vitamin B5 and vitamin B6 and a magnesium-containing organic or inorganic compound; wherein said hydrolyzed gelatin has a mean molecular weight range of from 2,000 to 100,000 Dalton; and wherein a daily dose of said treatment composition includes an effective amount of said hydrolyzed gelatin in a range of from 0.01 to 2 g per kilogram of body mass of the mammal, from 0.002 mg to 1 mg per kilogram of said body mass of each of said vitamin B1, said vitamin B2, said vitamin B5 and said vitamin B6 and from 0.25 mg to 15 mg of magnesium in said magnesium-containing organic or inorganic compound per kilogram of said body mass.

8. A method of reducing sports' injuries in an individual practicing a sport, said method comprising orally administering an effective amount of a composition to the individual once each day during a training period of the individual practicing the sport, said composition containing an effective amount of hydrolyzed gelatin in a range of from 0.01 g to 2 g per kilogram of body mass of the individual; from 0.002 mg to 1 mg of each of a plurality of B-group vitamins, each being selected from the group consisting of vitamin B1, vitamin B2, vitamin B5 and vitamin B6, per kilogram of said body mass of the individual; and from 0.25 mg to 15 mg of magnesium in a magnesium-containing organic or inorganic compound per kilogram of said body mass; wherein said hydrolyzed gelatin has a mean molecular weight range of from 2,000 to 50,000 Dalton.

* * * * *